United States Patent [19]

Maes

[11] 4,226,693
[45] Oct. 7, 1980

[54] CORROSION PROBE COMBINATION

[75] Inventor: Jean P. Maes, Merelbeke, Belgium

[73] Assignee: s.a. Texaco Belgium n.v., Brussels, Belgium

[21] Appl. No.: 974,597

[22] Filed: Dec. 29, 1978

[51] Int. Cl.² .......................................... G01N 27/46
[52] U.S. Cl. ............................... 204/195 C; 204/1 T; 73/86; 324/65 CR; 422/53
[58] Field of Search .......................... 204/1 C, 195 C; 136/203, 230; 73/86, 335, 336.5; 422/53; 324/65 CR; 62/3

[56] References Cited

U.S. PATENT DOCUMENTS

| | | | |
|---|---|---|---|
| 2,959,017 | 11/1960 | Gilman et al. | 62/3 |
| 3,319,457 | 5/1967 | Leone | 73/17 |
| 3,561,109 | 2/1971 | Puder | 29/573 |
| 3,627,493 | 12/1971 | Manley | 422/53 |
| 3,861,876 | 1/1975 | Robertson et al. | 23/230 C |
| 3,960,496 | 6/1976 | Schieber | 422/53 |
| 4,098,662 | 7/1978 | Schell et al. | 204/195 C |

OTHER PUBLICATIONS

G. R. Peacock, "The Land Dewpoint Meter Uses an Old Principle to Provide New Measurements in Waste & Process Gases", Presented at Instrument Society of America ISA-76 Conference, Houston, Texas, Oct. 1976.

*Primary Examiner*—Aaron Weisstuch
*Attorney, Agent, or Firm*—Carl G. Ries; Robert A. Kulason; Henry C. Dearborn

[57] ABSTRACT

A combined temperature control is an integral part of a corrosion probe. The probe includes a corrosion measuring element as one part thereof. The integral temperature control portion acts to provide a desired temperature at the measuring element. And, the result permits creation of the worst corrosive conditions at the measuring element of the probe, irrespective of the location of the probe in the corrosive environment.

3 Claims, 9 Drawing Figures

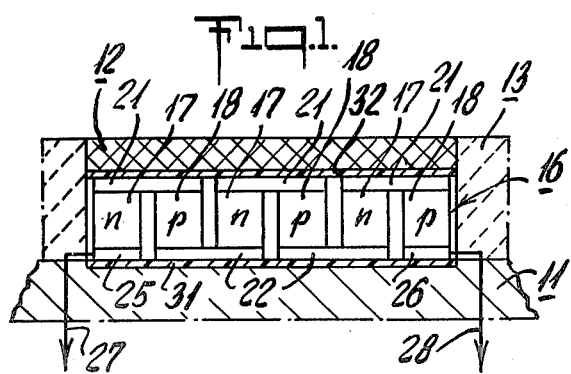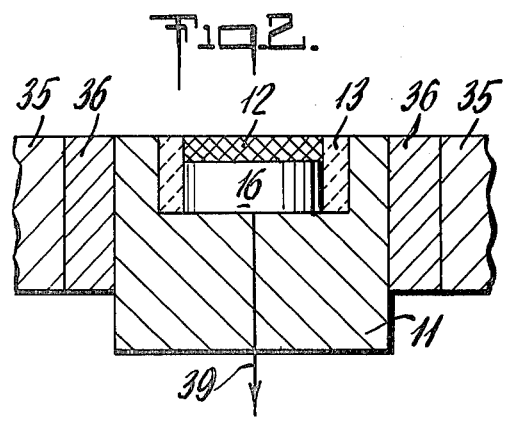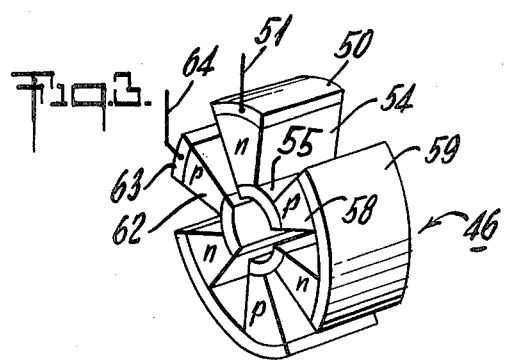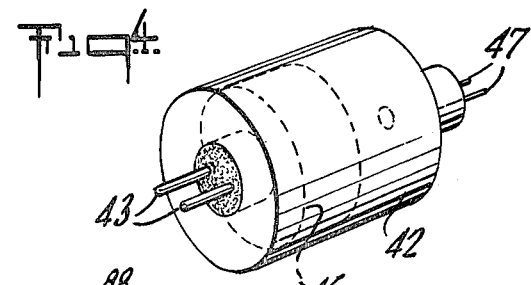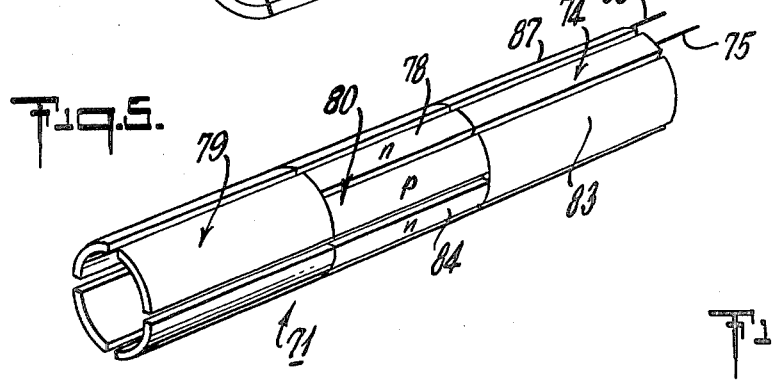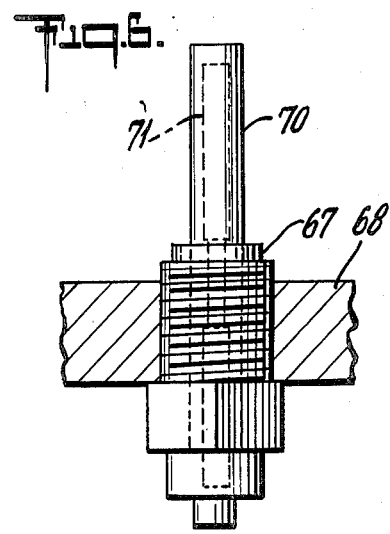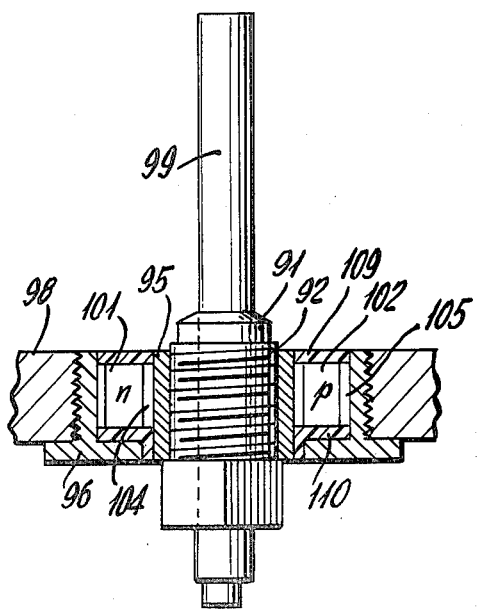

CORROSION PROBE COMBINATION

BACKGROUND OF THE INVENTION

1. Field of the Invention

This invention concerns corrosion detection in general. More specifically, it deals with an improved combination of a corrosion detection probe and a temperature control. The combination provides an ability to obtain maximum corrosive conditions at the location of a corrosion probe.

2. Description of the Prior Art

Different types of instruments have heretofore been used to measure the corrosion rate of various metals. Some of these instruments make use of electrochemical properties of the metal in an electrically conductive corrosive. Other instruments employ different testing techniques that measure electrochemical properties to monitor the corrosion rates. These latter are generally referred to as polarization, galvanic couples, and corrosion potential methods. Other instruments measure corrosion rate by monitoring the increase of electrical resistance of an exposed sample, or measuring element.

All of the foregoing techniques use corrosion probes that expose one or more metal coupons, or test specimens to the corrosive medium being studied (or measured). Such coupons are connected in an electric circuit so that either the electrochemical properties or the change in electrical resistance can be observed and employed to determine the rate of corrosion. However, it has been found that incorrect positioning of the probe or probes with regard to the local corrosive conditions in various types of equipment has led to misleading and incorrect corrosion rate measurement.

One prior attempt to eliminate such inaccuracies has been to employ a flush mounted electrode structure. For example, see that described in the U.S. Pat. No. 3,948,744, to R. H. Cushing, issued Apr. 6, 1976. Still, probe location has remained a very serious problem. Thus, in processes where temperature and pressure conditions are such that condensation or evaporation of corrosive is possible in certain regions of the process, the corrosion will tend to be localized in such regions. Furthermore, since the locations of these regions are generally not predictable, a corrosion probe may very likely not be located at such a region and consequently it would miss the corrosion phenomenon.

Because the foregoing conditions have existed, it has been found that failures may occur with catastrophic results, while the corrosion rate measurement being affected had not indicated any danger. Thus, small amounts of condensed water accumulating acid components has caused severe localized corrosion in the upper parts of a distillation column and an overhead system of a petroleum type plant. Also, in many other process operations in the petroleum industry, severe corrosion problems may be met when handling vapors near dew point temperatures. Therefore, effective control of corrosion in such cases can only be realized by use of corrosion probes which create regions with temperatures at which condensation or evaporation may occur.

Consequently, it is an object of this invention to provide means for controlling the temperature of a measuring element (or coupon), compared to that of the surrounding metal of a corrosion probe. Also, the means may include probe temperature measurement and remote electrical operation.

Another object of the invention is to teach a method of making corrosion measurements. It comprises the steps of locating a probe within a container having a corrosive atmosphere therein, and regulating the temperature of a measuring element of the probe to produce maximum corrosive conditions at that location.

SUMMARY OF THE INVENTION

Briefly, the invention concerns the combination of a corrosion probe having a measuring element adapted for being subjected to corrosive conditions, and a body for supporting said measuring element. And, the combination includes integral means for regulating the temperature of said measuring element to create maximum corrosive conditions.

Again briefly, the invention concerns the combination which comprises a corrosion probe having a measuring element adapted for being subjected to corrosive conditions and a body for supporting said measuring element. The combination also comprises thermoelectric means comprising a plurality of n-type and p-type semiconductors arranged for a Peltier-effect. The semiconductors have one group of electrodes in thermal contact with said measuring element, and another group of electrodes in thermal contact with said probe body. It also comprises thermal insulating means for separating said two groups of electrodes, and first circuit means having two connections for applying an e.m.f. to and receiving an e.m.f. from said electrodes. It also comprises a thermocouple for measuring the temperature of said measuring element, and a differential amplifier having two inputs and an output. Also, it comprises a potentiometer, and second circuit means for connecting the output of said potentiometer to one input of said amplifier, and third circuit means for connecting said thermocouple in series between the other input of said amplifier and one connection of said first circuit means. It also comprises fourth circuit means for connecting the output of said amplifier to the other connection of said first circuit means. All of the foregoing is in cooperation, whereby the temperature of said probe measuring element may be regulated in accordance with said potentiometer setting.

Once more briefly, the invention concerns a method of making corrosion measurements which comprises the steps of locating a probe in the wall of a container, and having a measuring element in a vaporous corrosive atmosphere in said container. It also comprises the steps of regulating the temperature of said measuring element to be lower than the temperature of said wall at said location of the probe, in order to cause condensation on said element. The said step of regulating the temperature comprises applying Peltier effect cooling to said measuring element relative to said container wall at said location, by mounting a plurality of n-type and p-type semiconductors in pairs at that location. One group of electrodes are in thermal contact with the measuring element, and another group of electrodes are in thermal contact with said container wall. It also comprises the step of connecting a DC e.m.f. to said groups of electrodes in order to cause current flow sufficient to cause said condensation.

BRIEF DESCRIPTION OF THE DRAWINGS

The foregoing and other objects and benefits of the invention will be more fully set forth below in connection with the best mode contemplated by the inventor of carrying out the invention, and in connection with which there are illustrations provided in the drawings, wherein:

FIG. 1 is a schematic representation of a group of semiconductor elements mounted in combination with a measuring element of a corrosion probe, in accordance with the invention;

FIG. 2 is a less enlarged schematic illustration, showing the entire corrosion probe in accordance with the FIG. 1 illustration and mounted in a container wall;

FIG. 3 is a schematic in perspective illustrating the manner in which a group of semiconductor elements with electrodes may be mounted for coaxial effects;

FIG. 4 is a schematic in perspective, illustrating a probe making use of the coaxial arrangement in accordance with FIG. 3;

FIG. 5 is another schematic in perspective, illustrating a manner of constructing Peltier-type semiconductor elements with the electrodes thereof in a cylindrical arrangement;

FIG. 6 is a schematic elevation partly in cross section, showing a probe making use of the cylindrical arrangement in accordance with FIG. 5;

FIG. 7 is a schematic elevation partly in cross section, showing an arrangement for applying the temperature control created by Peltier effect semiconductors to an existing corrosion probe structure;

DESCRIPTION OF THE PREFERRED EMBODIMENTS

Figure 8:
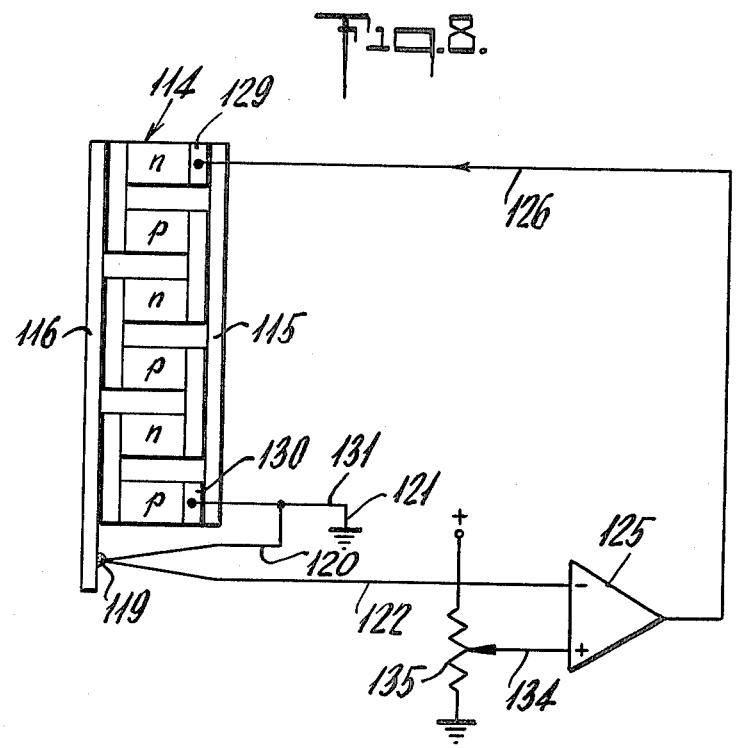
FIG. 8 is a schematic electrical circuit diagram illustrating a control system for the temperature in accordance with a predetermined setting.

Combinations according to this invention feature controlled temperature of the measuring element of a corrosion probe compared to that of the surrounding material, i.e. the body of the probe. Also, they feature probe temperature measurement with remote electrical operation.

In addition, combinations according to this invention expand the possible applications of the type of corrosion rate measuring probes that act on the electrochemical properties of the metal. Such probes require the presence of an electrically conductive corrosive, so that they heretofore were not used in vapor systems. However, this invention permits and provides conditions such that condensate may accumulate on the electrode surfaces which are cooled below the dew point. Thus a conductive medium is provided. And, it may be noted that a flush mounted electrode structure would, of course, be preferable for such application.

FIGS. 1 and 2 are schematic illustrations showing the elements of a combination according to the invention where the measuring element of a probe is flush mounted with the wall of a container with a corrosive atmosphere therein. Thus, a probe body 11 is indicated. The probe has a measuring element 12 which is surrounded by a thermally insulating layer 13.

Mounted beneath the measuring element 12, and in thermal contact therewith, there is a thermo-element 16 which acts to control and/or measure the temperature difference between the measuring element 12 and the probe body 11. As illustrated in FIG. 1, this thermo-element structure preferably is in the form schematically indicated. That is, it has a plurality of n-type semiconductors 17 connected in series with a like plurality of p-type semiconductors 18. There are three electrodes 21 above the two electrodes 22 beneath (as viewed in FIG. 1) which connect alternate sides of the semiconductors 17 and 18 together. This provides a Peltier effect temperature transfer when an e.m.f. is applied between end electrodes 25 and 26. The latter electrodes have electrical circuit connections 27 and 28, respectively, attached thereto.

There are thin, electrically insulating layers 31 and 32 between the body 11 and the thermo-element 16, and between the measuring element 12 and the thermo-element 16, respectively. The insulating layer 31 is between the electrodes 22, 25 and 26 and the probe body 11 on the bottom, and the layer 32 is between the electrodes 21 and the measuring element 12 on the top, both as viewed in FIG. 1. It should be noted that these electrically insulating layers 31 and 32 are thin and designed to permit thermal contact between the electrodes 21 and the measuring element 12 at the top, and between the electrodes 22, 25 and 26 and the body 11 at the bottom.

It will be understood that the FIG. 2 illustration indicates the mounting of the probe body 11 in a wall 35 of a pipe or vessel which contains a corrosive atmosphere therein. It will also be understood that the body 11 of the probe may have an attaching structure 36 which is schematically indicated. It is for mounting the probe body 11 in the wall 35 of the container. It will be noted that the necessary electrical connections are only schematically shown, i.e. by a connection 39 in FIG. 2. This encompasses a connecting cable that, of course, would include the electrical circuit connections 27 and 28 in addition to electrical circuit elements (not shown) for the probe structure.

FIGS. 3 and 4 illustrate a modification of the invention wherein the thermo-element structural arrangement is such as to have it coaxial with the probe structure.

FIG. 4 shows a probe body 42 which includes a pair of measuring elements 43 that are supported in any feasible manner for the type of probe that is being employed which is in a coaxial arrangement within a thermo-element unit 46. Electrical circuit connections 47 are schematically indicated. They, of course, include probe circuit connectors (not shown) as well as the circuit connections for the thermocouple unit 46, which are indicated below.

In the modification according to FIGS. 3 and 4, the thermo-element structure is illustrated in FIG. 3. It includes an electrode 50 which has a circuit connection 51 attached thereto. The electrode 50 is on one side of an n-type semiconductor 54 that has an inner electrode 55 on the other side thereof. Electrode 55 is in common with one side of a p-type semiconductor 58 that has another electrode 59 on the other side thereof. It will be clear that there is a series of the n-type and p-type semiconductors that are connected in a continuing arrangement ending with a p-type semiconductor 62 that has an electrode 63, with a circuit connection 64 attached thereto.

It will be understood that the arrangement is similar in principle to that of the FIGS. 1 and 2 modification, so that the thermo-element unit 46 of FIGS. 3 and 4 will have one set of electrodes in thermal contact with the measuring elements 43 of the probe. The other set of electrodes are in thermal contact with the body 42 of the probe.

Another modification is illustrated in FIGS. 5 and 6. In this case the structural arrangement of the thermocouple unit may be termed a cylindrical arrangement. Thus, as schematically illustrated in FIG. 6, there is a probe 67 that is mounted in a wall 68 of a container having a corrosive atmosphere therein. A measuring element 70 extends from the probe 67 into the corrosive atmosphere, and a cylindrical thermo-element unit 71 is mounted therein. In this case the thermo-element unit is made up with an electrode 74 that has a circuit connection 75 attached thereto. The electrode is on one end of an n-type semiconductor 78. The other side of the semiconductor 78 connects with an electrode 79 that is in common with one side of a p-type semiconductor 80. Another electrode 83 connects with the other side of p-type semiconductor 80 and one side of an n-type semiconductor 84. The arrangement continues around in a manner similar to that described above in connection with the FIG. 3 thermo-element unit 46, so that the other end of the series of semiconductors terminates at an electrode 87 with a circuit connection 88 attached thereto.

FIG. 7 illustrates a combination according to the invention that may be employed where an existing corrosion probe is adapted to receive a thermo-element so as to provide the desired temperature control according to this invention. A corrosion probe 91 is provided with a threaded nipple portion 92 for screwing it into an inner sleeve 95 of a thermo-element holder 96. The holder 96 in its turn, threads into a wall 98 of a container for a corrosive atmosphere that is to be measured by a measuring element 99 of the probe 91. Within the holder 96 there is a thermo-element array that is coaxial relative to the probe. Thus, this array is like that of FIG. 3. It includes plural n-type semiconductors 101, and p-type semiconductors 102. It will be understood that these are coaxially arranged with the probe 91, and that inner electrodes 104 are in thermal contact with the sleeve 95. Similarly outer electrodes 105 are in thermal contact with the holder 96 which is, of course, in good thermal contact with the wall 98 of the container.

It will be appreciated by one skilled in the art that with the construction illustrated by FIG. 7 the thermocouple unit will need to be designed with greater power than the modifications illustrated in the FIGS. 1-6 showings. Also, it may be observed that the thermocouple unit is supported between thermally insulating members 109 and 110 so that the heat transfer carried out by the thermo-element unit (the n-type and the p-type semiconductor elements) will go from the sleeve 95 to the holder 96. Also, it will be understood that the required electrical circuit connections (not shown) will be included so as to connect the thermo-element elements to a source of e.m.f., and also to make the required circuit connections for the probe 91.

Figure 9:
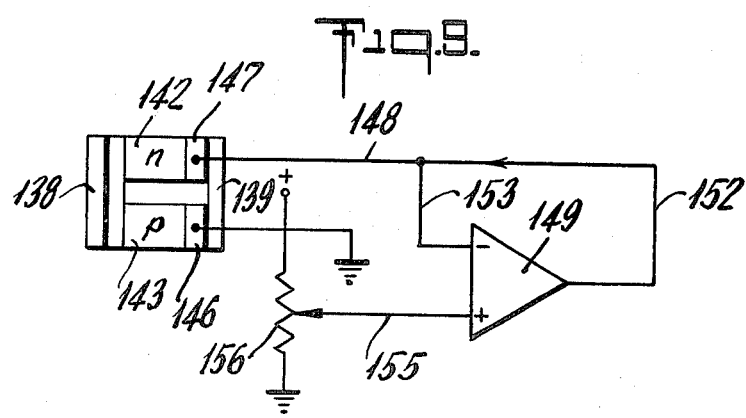
FIG. 9 is another schematic electrical circuit diagram illustrating a temperature control system similar to FIG. 8, but eliminating the use of a separate thermocouple for temperature measurement.

FIGS. 8 and 9 show circuit diagrams to illustrate a manner of regulating the temperature as determined by a Peltier type thermo-element. It will be understood that the particular configuration of the thermo-element elements might take any of the various forms illustrated and described above in connection with the FIGS. 1-7. Or, the configuration might comprise some other arrangement (not shown) which might suggest itself to one skilled in the art.

In FIG. 8 there is a series of Peltier effect semiconductor elements 114 that are connected in a series group as indicated. They are situated between heat conductive elements 115 and 116 that are to have a heat transfer from one to the other. There is a thermocouple junction 119 that acts to develop an e.m.f. in dependence upon the difference in temperature between the heat conductive element 116 and the end of a conductor 120 that makes up one of the leads to the thermocouple junction 119. This e.m.f. is developed between a ground circuit 121 and another conductor 122 that is connected to the other side of the junction 119. Conductor 122 goes to one input of an operational amplifier 125, and the output of the amplifier goes over a circuit connection 126 to an electrode 129 of the Peltier elements 114. At the other end of the Peltier elements 114 an electrode 130 is connected to the ground 121 via a conductor 131.

The amplifier 125 has a second input connection 134 that goes to a potentiometer 135 so that a predetermined voltage input may be applied to the amplifier 125. It will be understood that this will produce a regulation of the amount of heat transfer by the Peltier elements 114, in accordance with the potentiometer input voltage.

FIG. 9 illustrates a simpler arrangement for providing control of the temperature difference. Thus, there are two heat conductive elements 138 and 139 which have a pair of Peltier effect semiconductor elements 142 and 143 connected as a thermocouple between them. In this case the thermo-element which is made up of the elements 142 and 143 will act both to measure the temperature difference between the elements 138 and 139, as well as to apply a heat transfer. Both are in accordance with the known Peltier effects. Consequently, this simplified arrangement eliminates the need for an extra thermocouple. It will be observed that one elecrrode 146 is connected to ground, as indicated, while another electrode 147 is connected via a circuit connection 148 both to the output of an operational amplifier 149 via a circuit connection 152 and to one input of the amplifier 149 via a circuit connection 153. The other input for the amplifier 149 is from a potentiometer 156 that may be adjusted to set a predetermined input voltage so that the system will automatically regulate the temperature difference between the elements 138 and 139 to be proportional to that predetermined input voltage from the potentiometer 156.

METHOD

The invention encompasses a method of making corrosion measurements, and this method comprises the following steps. A first step is that of locating a probe in the wall of a container. Such probe will have a measuring element that is in a vaporous corrosive atmosphere in the container. This step is illustrated, by way of example, in FIG. 2 where the probe 11 is located in the wall 35 of a container that has a vaporous corrosive atmosphere on the side that is in contact with the measuring element 12.

A second step is that of regulating the temperature of the measuring element so as to make it lower than the temperature of the container wall at the location of the probe. This is in order to cause condensation on the measuring element. It may be carried out by various and different systems. For example, the circuit arrangements illustrated by FIGS. 8 and 9 may be employed to create the temperature effects at the measuring element 12 which is indicated in FIG. 2. When carried out in such manner, the step includes the application of Peltier effect cooling to the measuring element, e.g. element 12 in FIGS. 1 and 2. This cooling is relative to the container wall at the location of the probe. Such application of the cooling effect involves the mounting of a plurality of n-type and p-type semiconductors in pairs, with one group of electrodes in thermal contact with the measuring element. Thus, the electrodes 21 in FIG. 1 are in thermal contact with the measuring element 12. The same pairs of semiconductors are also mounted with the other group of electrodes 22, 25 and 26 thereof in thermal contact with the container wall. The latter is indicated in the FIGS. 1 and 2 illustrations which show the body 11 of the probe in heat conductive relationship with the container wall 35, via the attaching structure 36.

The temperature regulating step using pairs of semiconductors, is completed by connecting a DC e.m.f. to the groups of electrodes. This is done so as to cause current flow which, by reason of the Peltier effect, is sufficient to cause the desired condensation temperature at the measuring element.

While particular embodiments of the invention have been described above in considerable detail, in accordance with the applicable statutes, this is not to be taken as in any way limiting the invention but merely as being descriptive thereof.

I claim:

1. The combination, comprising
   a corrosion probe having a measuring element adapted for being subjected to corrosive conditions and a body for supporting said measuring element,
   thermoelectric means comprising a plurality of n-type and p-type semiconductors arranged for a Peltier-effect and having one group of electrodes in thermal contact with said measuring element and another group of electrodes in thermal contact with said probe body,
   thermal insulating means for separating said two groups of electrodes,
   first circuit means having two connections for applying an emf to and receiving an emf from said electrodes,
   a thermocouple for measuring the temperature of said measuring element,
   a differential amplifier having two inputs and an output,
   a potentiometer,
   second circuit means for connecting the output of said potentiometer to one input of said amplifier,
   third circuit means for connecting said thermocouple in series between the other input of said amplifier and one connection of said first circuit means, and
   fourth circuit means for connecting the output of said amplifier to the other connection of said first circuit means,
   all whereby the temperature of said probe measuring element may be regulated in accordance with said potentiometer setting.

2. In combination,
   a corrosion probe having a measuring element adapted for being subjected to corrosive conditions and a body for supporting said measuring element, and
   integral thermo-electric Peltier effect means for regulating the temperature of said measuring element comprising a plurality of n-type and p-type semiconductors associated with said probe in thermal contact with said measuring element,
   means for measuring the temperature difference between said measuring element and said probe body and producing an emf in accordance therewith,
   means for opposing said emf at a predetermined amplitude in accordance with a desired temperature difference,
   means for amplifying the difference between said emf and said opposing means, and
   circuit means for applying the output of said amplifying means to said plurality of n-type and p-type semiconductors for regulating said temperature difference to maintain it at said desired amount.

3. In combination, a corrosion probe having a measuring element adapted for being subjected to corrosive conditions and a body for supporting said measuring element, thermoelectric Peltier-effect means comprising a plurality of n-type and p-type semiconductors and having one group of electrodes in thermal contact with said measuring element and another group of electrodes in thermal contact with said body,
   thermal insulating means for separating said two groups of electrodes,
   circuit means for applying an emf to said electrodes for activating said Peltier-effect means to regulate the temperature of said measuring element, comprising
   a differential amplifier,
   means for connecting one of said groups of electrodes to an input of said amplifier,
   means for connecting an adjustable emf to the other input of said amplifier, and
   means for connecting the output of said amplifier to the other said groups electrodes, whereby the temperature of said measuring element may be regulated by adjustment of said adjustable emf.

* * * * *